United States Patent [19]

Cairns et al.

[11] 4,055,654
[45] * Oct. 25, 1977

[54] 6,8-DI-T-BUTYL-4-OXO-4H-1-BENZOPYRAN-2-CARBOXYLIC ACID AND DERIVATIVE FOR THE PREVENTION OF ASTHMATIC SYMPTOMS

[75] Inventors: Hugh Cairns; Albert Chambers; Thomas Brian Lee, all of Loughborough, England

[73] Assignee: Fisons Limited, England

[*] Notice: The portion of the term of this patent subsequent to Apr. 20, 1993, has been disclaimed.

[21] Appl. No.: 646,025

[22] Filed: Jan. 2, 1976

Related U.S. Application Data

[62] Division of Ser. No. 382,642, July 26, 1973, Pat. No. 3,952,104, which is a division of Ser. No. 172,214, Aug. 16, 1971, Pat. No. 3,786,071.

[30] Foreign Application Priority Data

Aug. 25, 1970  United Kingdom ............... 40777/70
Sept. 15, 1970  United Kingdom ............... 43984/70
Dec. 11, 1970  United Kingdom ............... 58860/70
June 3, 1971  United Kingdom ............... 18807/71

[51] Int. Cl.² ........................................... A61K 31/35
[52] U.S. Cl. .................................................. 424/283
[58] Field of Search ........................................ 424/283

[56] References Cited

U.S. PATENT DOCUMENTS

| 3,427,324 | 2/1969 | Fitzmaurice | 424/283 |
| 3,484,445 | 12/1969 | Lee et al. | 424/283 |
| 3,629,290 | 12/1971 | Cairns et al. | 424/283 |
| 3,652,765 | 3/1972 | Ellis et al. | 424/283 |
| 3,816,470 | 6/1974 | Tronche et al. | 424/283 |
| 3,864,493 | 2/1975 | Cairns et al. | 424/283 |
| 3,952,013 | 4/1976 | Hazard et al. | 424/283 |

Primary Examiner—Norman A. Drezin
Attorney, Agent, or Firm—Wendroth, Lind & Ponack

[57] ABSTRACT

There are described certain mono-chromone-2-carboxylic acids of formula,

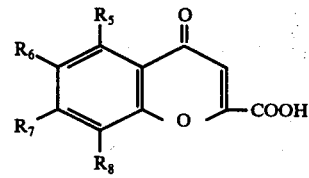

having one substituent in the 5 or 6 position or having 2 or more substituents in the 5,6,7 or 8 positions. There are also described processes for making the compounds and pharmaceutical compositions, for the treatment of asthma, containing the compounds.

4 Claims, No Drawings

6,8-DI-T-BUTYL-4-OXO-4H-1-BENZOPYRAN-2-CARBOXYLIC ACID AND DERIVATIVE FOR THE PREVENTION OF ASTHMATIC SYMPTOMS

This is a division of Ser. No. 382,642, filed July 26, 1973, now U.S. Pat. No. 3,952,104, which in turn is a division of Ser. No. 172,214, filed Aug. 16, 1971, now U.S. Pat. No. 3,786,071.

This invention relates to new compounds, methods for their preparation and compositions containing them.

According to our invention we provide compounds of formula I,

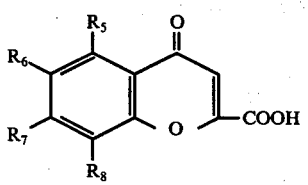

in which $R_5$ represents hydrogen, hydroxy, or $-OR_5'$ in which $R_5'$ is a straight or branched saturated, or ethylenically unsaturated, hydrocarbon group which group is optionally substituted by an $-OH$ or by a 5 or 6 membered oxygen-containing heterocyclic ring, $R_5'$ together with any substituents thereon containing from 3 to 8 carbon atoms inclusive, $R_6$ represents hydrogen, alkyl containing from 1 to 6 carbon atoms inclusive, alkenyl containing from 2 to 6 carbon atoms inclusive, or phenyl, $R_7$ represents hydrogen or lower alkoxy — lower alkoxy, $R_8$ represents hydrogen, alkyl containing from 1 to 6 carbon atoms inclusive, or alkenyl containing from 2 to 6 carbon atoms inclusive, provided that
i. $R_8$ does not represent propyl when $R_5$ represents hydroxy-propoxy,
ii. $R_8$ does not represent ethyl when $R_5$ is but-3-enoxy,
iii. two or three of $R_5$, $R_6$, $R_7$ and $R_8$ are other than hydrogen, save that when
   a. $R_5'$ represents a straight chain alkyl or alkenyl group containing from 5 to 7 carbon atoms or a branched chain alkyl or alkenyl group containing from 5 to 8 carbon atoms, or b. $R_6$ represents phenyl,
none, one or two of $R_6$, $R_7$ and $R_8$ are other than hydrogen.
iv. $R_6$ and $R_8$ are both ethyl or are both sec. butyl only when $R_5$ is not hydrogen,
v. $R_6$ is alkyl containing from 4 to 6 carbon atoms when $R_7$ is lower alkoxy — lower alkoxy, and
vi. at least one of $R_6$ and $R_8$ contains 2 or more carbon atoms when $R_5$ is hydrogen or hydroxy,
and pharmaceutically acceptable derivatives thereof.

According to our invention we also provide a process for the production of a compound of formula I, or a pharmaceutically acceptable derivative thereof, which comprises,
a. cyclising a compound of formula II,

II

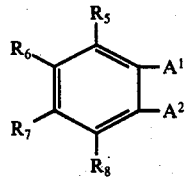

in which $R_5$, $R_6$, $R_7$, $R_8$ and the provisos are as defined above, and $A^1$ and $A^2$ represent the pairs of groups
i. $-OOCH_2COCOR''$ and $-OM$, or
ii. $-H$ and $-O-C(COOM)=CH-COOM$
in which $R''$ represents $-OM$, or a group which is hydrolysable thereto, and
M represents hydrogen or an alkali metal, and if necessary or desired hydrolysing the group $R''$,
b. selectively hydrolysing or oxidising a compound of formula III,

III

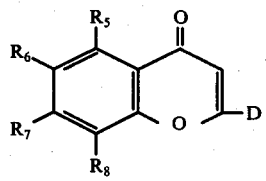

in which $R_5$, $R_6$, $R_7$, $R_8$ and the provisos are as defined above, and D is a group which is hydrolysable or oxidasable to a $-COOH$ group,
provided that when D is a group oxidisable to a $-OOOH$ group none of $R_5$, $R_6$, $R_7$ and $R_8$ represent a alkyl group other than a t-butyl group,
c. selectively dehydrogenating a compound of formula IV,

IV

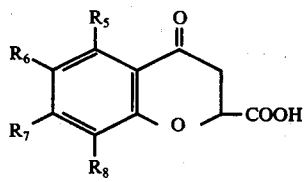

or an ester thereof in which $R_5$, $R_6$, $R_7$, $R_8$ and the provisos are as defined above,
d. producing a compound of formula Ia, Ia

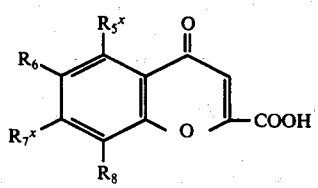

or an ester thereof in which $R_6$, $R_8$ and the provisos are as defined above,
$R_5^x$ is hydrogen, or $-OR_5'$ as defined above,
$R_7^x$ has the same significances as $R_7$ above,
and one of $R_5^x$ and $R_7^x$ is $-OR_5'$ or lower alkoxy — lower alkoxy respectively,
by reacting a corresponding compound of formula V,

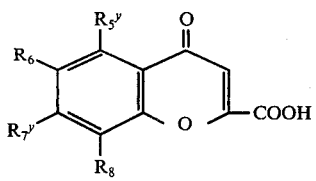

or an ester thereof in which $R_6$, $R_8$ and the provisos are as defined above, $R_5{}^y$ is hydrogen or hydroxy, $R_7{}^y$ is hydrogen, hydroxy, hydroxy-lower-alkoxy, or lower alkoxy substituted by a good leaving group, and one of $R_5{}^y$ and $R_7{}^y$ is hydroxy, hydroxy-lower alkoxy, or lower alkoxy substituted by a good leaving group, with, when $R_5{}^y$ is a hydroxy group, an appropriate alkylene oxide, or a compound of formula XIV, $$R_5'\text{—X} \qquad \text{XIV}$$

in which $R_5'$ is as defined above, and

X represents a good leaving group;

when $R_7{}^y$ is hydroxy lower alkoxy, a lower alkane substituted by a good leaving group; or when $R_7{}^y$ is lower alkoxy substituted by a good leaving group, a lower alkanol, or when $R_7{}^y$ is hydroxy, lower alkoxy - lower alkane substituted by a good leaving group;

e. producing a compound of formula Ib,

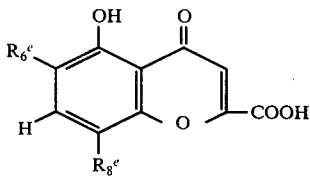

or an ester thereof in which the provisos are as defined above, $R_6{}^e$ and $R_8{}^e$ have the same significances as $R_6$ and $R_8$ above, save that at least one of $R_6{}^e$ and $R_6{}^e$ represent a group $R_{11}$, and $R_{11}$ represents an allyl group or an allyl group substituted by alkyl in the postion adjacent to the benzene ring, said group containing up to 6 carbon atoms, by subjecting a compound of formula XII,

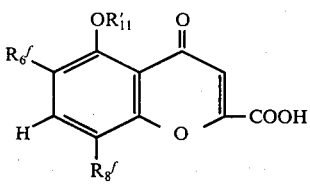

or an ester thereof in which the provisos are as defined above, $R_{11}'$ represents an allyl group or an alkyl substituted allyl group containing up to 6 carbon atoms, and $R_6{}^f$ and $R_8{}^f$ have the same significance as $R_6$, and $R_8$ above, save that at least one of $R_6{}^f$ and $R_8{}^f$ represents hydrogen, to an elevated temperature, f. producing a compound of formula If

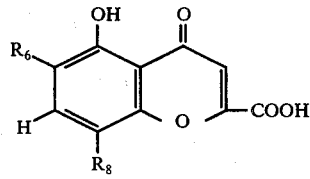

or an ester thereof in which $R_6$, $R_7$, $R_8$ and the provisos are as defined above, By replacing an $R^9$ group with a hydrogen atom in a compound of formula XIII,

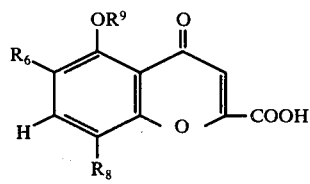

or an ester thereof, in which $R_6$, $R_7$, $R_8$ and the provisos are as defined above, and $R^9$ represents alkyl, aralkyl or acyl, or g. producing a compound of formula Ig,

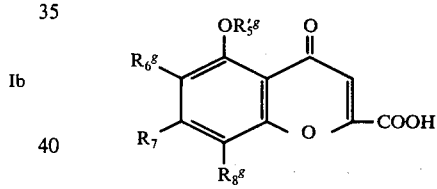

or an ester thereof in which $R_7$ and the provisos are as defined above, and $R_6{}^g$, $R_5'{}^g$ and $R_8{}^g$ have the same significances as $R_6$, $R_5'$ and $R_8$ respectively, save that at least one of $R_6{}^g$, $R_5'{}^g$ and $R_8{}^g$ represent alkyl containing from 2 to 6 carbon atoms, by hydrogenating a corresponding compound of formula XV,

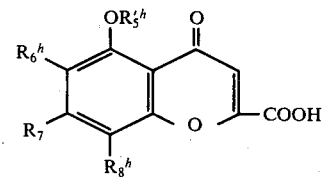

or an ester thereof, in which $R_7$ and the provisos are as defined above, and $R_6{}^h$, $R_8{}^h$ and $R_5'{}^h$ have the ame significance as $R_6$, $R_8$ and $R_5'$ above, save that at least one of $R_6{}^h$, $R_8{}^h$ and $R_5'{}^h$ represent an alkenyl group containing from 2 to 8 carbon atoms as appropriate, and if necessary or desired hydroysing the ester of the compound of formula I to a compound of formula I and/or converting the compound of formula I to a pharmaceutically acceptable derivative thereof.

The cyclisation of process (a) (i) may be carried ou by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150°C. The group —COR' is preferably an ester group, e.g. R" may be a lower alkoxy group.

The cyclisation of process (a) (ii) may be carried out by treating the appropriate compound of formula II with a cyclising agent, for example a dehydrating agent such as chlorosulphonic, polyphosphoric or sulphuric acid. The reaction is preferably carried out under anhydrous conditions and may be carried out at a temperature of from about 0° to 100°C. Alteratively cyclisation may be achieved by converting the free carboxy groups of the compound of formula II to acyl halide groups and subjecting the resulting acyl halide to an intromolecular Friedel-Crafts reaction.

In process (b) the group D may be, for example an ester, acid halide, amide or a nitrile group, which may be hydrolysed to a —OOOH group. The hydrolysis may be carried out using conventional techniques, for example under mildly basic conditions, e.g. using sodium carbonate, sodium bicarbonate, or under acidic conditions, e.g. a mixture of aqueous dioxan and dichloric acid, or hydrogen bromide in acetic acid. The hydrolysis may be carried out at a temperature of from about 25° to 120° depending on the compounds used. Alternatively the group D may be an alkyl, e.g. a lower alkyl such as methyl, an aralkenyl, e.g. styryl, an acyl, e.g. a lower alkanoyl such as acetyl, or an aldehyde, e.g. formyl group. Theoxidation may be carried out using conventional techniques which do not otherwise modify the molecule, for example, an alkyl group may be oxidised using selenium dioxide, e.g. under reflux in aqueous dioxan; or chromic acid, e.g. under reflux in aqueous acetic acid. Aralkenyl groups may be oxidised using, for example neutral or alkaline potassium permanganate in aqueous ethanol, and acyl groups may be oxidised using, for example chromic acid or an aqueous hypochlorite, e.g. sodium hypochlorite. Aldehyde groups may be oxidised using, for example chromic acid or silver oxide.

In process (c) the dehydrogenation may be carried out by oxidation using a mild oxidising agent, for example selenium dioxide, palladium black or chloranil, lead tetraacetate or triphenyl methyl perchlorate. Alternatively the dehydrogenation may be carried out indirectly by halogenation followed by dehydrohalogenation, e.g. by treatment with N-bromosuccinimide or pyridinium bromide perbromide to yield the 3-bromo derivative which is subsequently dehydrobrominated. The reaction may be carried out in a solvent which is inert under the reaction conditions, e.g. a halogenated hydrocarbon, xylene, or glacial acetic acid. The reaction may be carried out at an elevated temperature, e.g. from 25° to 150°C.

In process d) the good leaving group X may be, for example, a halide, e.g. a bromide or iodide, or an alkyl or aryl sulphonate, e.g. a methane sulphonate group. The reaction may be carried out in a solvent which is inert under the reaction conditions, e.g. a lower alkanol, a ketone such as acetone or isobutylmethyl ketone, or dimethylformamide. The reaction may also be carried out in the presence of an acid binding agent, e.g. potassium carbonate, and optionally also in the presence of a catalyst, e.g. potassium iodide; suitably the reaction is carriedout at a temperature of 25° to 150°C. Alternatively process d) may be carried out using the compound of formula 4(or preferably an ester thereof), in the form of a thallium salt of the reactive hydroxy group. When a thallium salt is used the reaction may be carried out at an elevated temperature and the product may be recovered from the reaction mixture by solvent extraction.

In process e) the reaction may be carried out under conditions conventional for a Claisen rearrangement, e.g. at a temperature of about 170° to 250°C optionally in a high boiling solvent which is inert under the reaction conditions, e.g. tetrahydronaphthalene or a dialkyl aniline.

In process f) the replacement of the group $-R^9$ by a hydrogen atom may be carried out when $R^9$ is an alkyl, e.g. a lower alkyl such as ethyl, or aralkyl, e.g. benzyl, group by using an acid, e.g. HCl in ethanol, aqueous HBr, or HBr in glcial acetic acid. Where $R^9$ is an acyl, e.g. a lower alkanoyl such as acetyl, group the reaction may be carried out under mild alkaline conditions and where $R^9$ is an aralkyl, e.g. a benzyl group, the reaction may be carried out by hydrogenation. The reaction may be carried out at an elevated temperature.

In process (g) the hydrogenation may be carried out using catalytic hydrogention, for example using a palladium on charcoal catalyst in a suitable solvent, e.g. ethanol. The reaction may conveniently be carried out at from about 20° to 80°C, preferably at slightly greater than atmospheric pressure.

In processes (c) (d) (e) (f) and (g) the ester may be, for example a lower alkyl ester.

The compounds of formula II in which $A^1$ and $A^2$ represent the pair of groups —OOOH₂OOCOR" and —OM may be made by reacting a compound of formula VII,

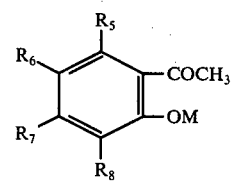

VII in which $R_5$, $R_6$, $R_7$, $R_8$, M and the provisos are as defined above, with a compound of formula VIII,

R'CZ—CZR"    VIII in which R" is as defined above,

R' is a group reactive with a hydrogen in the —COCH₃ group of the compound of formula VII, e.g. an alkoxy, halo, amino, alkylamino, substituted amino (e.g. an arylsulphonylamino group) or substituted alkylamino group, each Z is a carbonyl oxygen atom, or one Z may represent two halogen atoms and the other a carbonyl oxygen atom, and if necessary hydrolysing the resulting compound to a compound of formula II. The preferred compounds of formula VIII are dialkyl oxalates, e.g. diethyl oxalate.

The compound of formula II in which $A^1$ and $A^2$ represent the pair of groups —H and —O—(-

COOM)=CH—OOOM may be made by reacting a compound of formula IX,

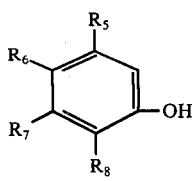

in which $R_5$, $R_6$, $R_7$, $R_8$ and the provisos are as defined above,
with a dialkyl acetylene dicarboxylate, in conventional manner, followed if necessary by hydrolysis.

The compounds of formula III may be made in a manner analogous to process (a) (i) using a starting material of formula X,

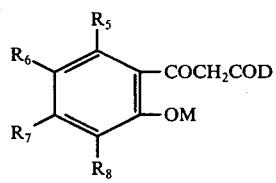

in which $R_5$, $R_6$, $R_7$, $R_8$, M and D are as defined above.

The compoundsof formula X may be made from known compounds in a manner analogous to thrat described above for the preparation of the corresponding compounds of formula II.

Alternatively the compounds of formula III may, for example in the case of the acid halide, the amide and the nitrile, be made from compounds of formula I using conventional techniques, e.g. reaction of an ester of the compound I with ammonia to produce the amide, followed by dehydration of the amide to form the nitrile.

The components of formula IV may be made by cyclising a compound of formula XI,

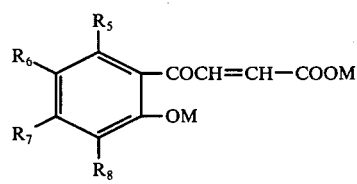

in which $R_5$, $R_6$, $R_7$, $R_8$, M and the provisos are as defined above,
by treating the compound of formula XI with a base in a solvent which is inert under the reaction conditions.

The compounds of formula XI may be made by reacting a compound of formula VII with glyoxalic acid or an ester thereof. Alternatively the compounds of formula XI may be made by reacting a compound of formula IX with maleic anhydride in a solvent in the presence of a Lewis acid, e.g. $AlCl_3$, and decomposition of the resulting complex with dilute acid.

The compounds of formula IV may also be made by selective hydrogenation of a corresponding compound of formula I.

The compounds of formulae V, XII, XIII and XV may be made from known compounds by processes analogous to process (a) above.

The compounds offormulae VII, VIII, IX and XIV are either known or may be made from known starting materials using conventional techniques.

The compounds of formula I and the intermeidates therefor may be isolated from their reaction mixtures using conventional techniques.

Pharmaceutically accpetable derivatives of the compounds of formula I include pharmaceutically accpetable salts, esters and amides of the 2-carboxylic acid group. Suitable salts include ammonium, alkali metal (e.g. sodium potassium and lithium) and alkaline earth metal salts (e.g. calcium or magnesium), and salts with suitable organic bases, e.g. salts with lower alkylanmines such as methylamine or ethylamine, with substituted lower alkylamines, e.g. hydroxy substituted alkylamines or with simple monocyclic nitrogen heterocyclic compounds, e.g. piperidine or morpholine. Suitable esters include simple lower alkyl esters, esters derived from alcohols containing basic groups, e.g. di-lower alkyl amino substituted alkanols, and acyloxy alkyl esters, e.g. a lower acyl-lower alkyl ester, or a bis-ester derived from a di-hydroxy compound, e.g. a di(hydroxy-lower alkyl) ether. The pharmaceutically acceptable salts of the basic esters, e.g. the hydrochloride, may also be used. The esters may be made by conventional techniques, e.g. esterification, transesterification or reaction of the acid, or a salt thereof, with an appropriate compound containing a good leaving group.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen e.g. the combination of reaginic antibody with specific antigen (see Example A). In man, both subjective and objective changes which result from the inhalation of specific antigen by sensitised subjects are inhibited by prior administration of the new compounds. Thus, the new compounds are useful in the treatment of asthma e.g. allergic asthma. The new compounds are also useful in the treatment of so-called "intrinsic" asthma (in which no sensitivity to extrinsic antigen can be demonstrated). The new compounds are also useful in the treatment of other conditions in which antigen-antibody reactions are responsible for disease, for example, hay fever, urticaria and certain other allergic skin diseases.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example A. For man the indicated total daily dosage is in the range of from about 1 mg to 3,500 mg which may be administered in divided doses from 1 to 6 times a day or in sustained release form. The unit dosage forms suitable for administration (by inhalation or oesophageally) comprise from about 0.17 mg to 600 mg of the compound admixed with a wolid of liquid pharmaceutically acceptable diluent, carrier or adjuvant.

The compounds of formula I, and pharmaceutically acceptable derivatives then of (and in particular the salts, e.g. the alkali metal salts, thereof) have the advantage that they are more readily absorbed and more active when administered cesophageally than compounds of similar structure to the compounds of formula I.

Preferred compounds of formula I are those in which $R_5$ is 3-methyl-n-buoxy, hydroxy or tetrehydrofurfuryloxy, $R_8$ is allyl, ethyl or propyl, $R_6$ is hydrogen, allyl or ethyl and $R_7$ is hydrogen. It is desirable in compounds of formula I that $R_5$, $R_6$, $R_7$ and $R_8$ together contain from 4 to 15 carbon atoms.

According to a specific feature of our invention we provide compounds of formula Ip, Ip in which $R_5^p$ represents hydrogen, a hydroxy group, a hydroxy propoxy group, or a 3-methyl-n-botoxy group,
$R_5^p$ represents hydrogen or an alkyl or alkenyl group containing from 2 to 6 carbon atoms,
$R_7^p$ represents hydrogen or a lower alkoxy-lower alkoxy group,
$R_8^p$ represents hydrogen or an alkyl or alkenyl group (other than an n - propyl group) containing from 2 to 6 carbon atoms, $R_8^p$ representing an alkenyl group when $R_5^p$ represents a hydroxy propoxy group,
two or three of $R_5$, $R_6$, $R_7$ and $R_8$ are other than hydrogen, save when $R_5$ represents a 2-methyl-n-butoxy group, and provides iv) v) and vi) are defined with respect to compounds of formula I.

According to another specific feature of our invention we provide compounds of formula Iq, Iq in which $R_5^q$ represents hydrogen, a hydroxy, a hydroxypropoxy, a branched chain alkoxy group containing from 5 to 8 carbon atoms, or a tetrahydrofurfuryloxy group,
$R_6^q$ represents hydrogen or an alkyl or alkenyl group containing from 2 to 6 carbon atoms,
$R_7^q$ represents hydrogen or a lower alkoxy-lower alkoxy group,
$R_8^q$ represents hydrogen or an alkyl or alkenyl group containing from 2 to 6 carbon atoms, $R_8^q$ representing an alkenyl group when $R_5^q$ represents a hydroxy-propoxy group,
two or three of $R_5^q$, $R_6^q$, $R_7^q$ and $R_8^q$ are other than hydrogen, save that when $R_5^q$ represents a branched chain alkoxy group containing from 5 to 8 carbon atoms, one, two or three of $R_5^q$, $R_6^q$, $R_7^q$ and $R_8^q$ may be other than hydrogen, and $R_6^q$ and $R_8^q$ are both ethyl only when $R_5^q$ is hydroxy, and provisos iii), iv), v) and vi) are as defined with respect to compounds of formula I.

According to yet another specific feature of our invention we provide compounds of formula Ir, Ir in which $R_5^r$ represents hydrogen, hydroxy or, $-OR_5'^r$ in which $R_5'^r$ contains from 3 to 8 carbon atoms inclusive, and is a straight or branched saturated, or ethylenically unsaturated, hydrocarbon group which group is optionally substituted by an $-OH$ or by a 5 or 6 membered oxygen containing heterocyclic ring,
$R_6^r$ represents hydrogen, alkyl containing from 1 to 6 carbon atoms inclusive, or alkenyl containing from 2 to 6 carbon atoms inclusive,
$R_7^r$ represents hydrogen or lower alkoxy - lower alkoxy,
$R_8^r$ represents hydrogen, alkyl containing from 1 to 6 carbon atoms inclusive, or alkenyl containing from 2 to 6 carbon atoms inclusive,
provided that (i) $R_8^r$ represents alkenyl when $R_5^r$ represents hydroxy-propoxy,
ii. $R_8^r$ does not represent ethyl when $R_5^r$ is but-3-enoxy,
iii. two or three of $R_5^r$, $R_6^r$, $R_7^r$ and $R_8^r$ are other than hydrogen, save that when $R_5'^r$ represents a straight chain alkyl or alkenyl group containing from 5 to 8 carbon atoms or a branched chain alkyl or alkenyl group containing from 6 to 8 carbon atoms, none, one or two of $R_6^r$, $R_7^r$, and $R_8^r$ are other than hydrogen,
iv. $R_6^r$ and $R_8^r$ are both ethyl or are both sec. butyl only when $R_5^r$ is not hydrogen,
v. $R_6^r$ is alkyl containing from 4 to 6 carbon atoms when $R_7^r$ is lower alkoxy - lower alkoxy, and
vi. at least one of $R_6^r$ and $R_8^r$ contains 2 or more carbon atoms when $R_5^r$ is hydrogen or hydroxy.

According to the invention there is also provided a process for the production of a pharmaceutically acceptable salt of a compound of formula I, which comprises treating a compound of formula Ic, Ic in which $R_5$, $R_6$, $R_7$, $R_8$ and the provisos are as defined above, and
E is a carboxylic acid group (or an ester thereof, or another salt thereof), a nitrile group, an acid halide group or an amide group,
with a compound containing an available pharmaceutically acceptable cation and capable of converting the group E to a pharmaceutically acceptable salt of a carboxylic acid group.

Compounds capable of converting the group E to a pharmaceutically acceptable salt of a carboxylic acid group include compounds, e.g. bases and ion exchange resins, containing pharmaceutically acceptable cations, e.g. sodium, potassium, calcium, ammonium and appropriate nitrogen containing organic cations. In general we prefer to form the pharmaceutically acceptable salt by treating the free acid of formula I with an appropriate base, e.g. with an alkaline-earth or alkali metal hydroxide, carbonate or bicarbonate in aqueous solution or by a metathetical process. When a strongly basic compound is uded care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

According to our invention we also provide a pharmaceutical composition comprising (preferably a minor proportion of) a compound of formula I, or a pharmaceutically acceptable derivative thereof, in combination with a pharmaceutically acceptable adjuvant, diluent or carrier. Examples of suitable adjuvants, diluents or carriers are:- for tablets and dragées; lactose, starch, talc or stearic acid; for capsules, tartaric acid or lactose; for suppositories; natural or hardened oils or waxes; for inhalation compositions, coarse lactose. For use in inhalation compositions the compound of formula I, or the pharmaceutically acceptable derivative thereof, preferably has a particle size of from 0.01 to 10 microns. The compositions may also contain suitable preserving, stabilising and wetting agents, solubilizers, sweetening andcolouring agents and flavourings. The compositions may, if desired, be formulated in sustained release form. We prefer compositions which are designed to be taken oesophageally and to release their contents in the gastrointestinal tract.

The invention is illustrated, but in no way limited by the following Examples, in which the parts are by weight, the molecular weights were obtained using a Perkin-Elmer RMU 6 Mass Spectrometer, the N.M.R. values were determined in deuterated dimethyl sulphoxide unless otherwise stated, the infra-red spectra were determined for potassium bromide discs and the temperatures are in °C.

EXAMPLE 1

8-Allyl-5-(2-hydroxypropoxy)-4-oxo-4H-1-benzopyran-2-carboxylic acid a.

3-Allyl-2-hydroxy-6-(2-hydroxypropoxy)acetophenone

A mixture of 58 parts of 3-allyl-2,6-dihydroxyacetophenone, 22.5 parts of propylene oxide and 0.25 parts of a 40% aqueous solution of benzyltrimethylammonium hydroxide in 70 parts of dioxan was heated in a sealed vessel at 100°C for 20 hours. The mixture was cooled and the vessel was opened. The dioxan was evaporated off and the residual oil was distilled to give 33 parts of 3-allyl-2-hydroxy-6-(2-hydroxypropoxy)acetophenone, boiling point, 158°–168°C/0.5-1.0 mm Hg., melting point 49°–51°C.

Analysis:
Found: C, 67.1; H, 7.20%;
$C_{14}H_{18}O_4$ requires: C, 67.2; H, 7.20%.

b.

8-Allyl-5-(2-hydroxypropoxy)-4-oxo-4H-1-benzopyran-2-carboxylic acid hemihydrate A solution of 50 parts of 3-allyl-2-hydroxy-6-(2-hydroxypropoxy)-acetophenone in 75 parts of diethyl oxalate was added to a stirred solution of sodium ethoxide prepared from the dissolution of 18.5 parts of sodium in 320 parts of ethanol. The resulting mixture was stirred and heated on a steam-bath for 3.5 hours, then most of the ethanol was evaporated off and the residue was diluted with 1000 parts of water and was washed with ether. The aqueous solution was acidified with concentrated hydrochloric acid then it was extracted with 3 lots of 250 parts of chloroform. Evaporation of the chloroform extract left a residue, which was heated under reflux for 30 minutes with 320 parts of ethanol and 5 parts of concentrated hydrochloric acid. The mixture was evaporated and the residue was agitated with 60 parts of ether to give a solid precipitate, which was filtered off, dissolved in bicarbonate solution and reprecipitated upon acidification. The crude product was dried, then dissolved in a 9/1 ether/petrol (b.p. 40°–60°C) mixture from which, by careful evaporation, there was obtained 7.4 parts of 8-allyl-5-(2-hydroxypropoxy)-4-oxo-4H-1-benzopyran-2-carboxylic acid hemihydrate, melting point 75°–80°C.

Analysis:
Found: C, 60.9; H, 5.46%;
$C_{16}H_{16}O_6 \cdot \frac{1}{2}H_2O$ requires: C, 61.3; H, 5.43%.
Mass Spectroscopy — Molecular Weight Found: 304; $C_{16}H_{16}O_6$ requires: 304.

c.

8-Allyl-5-(2-hydroxypropoxy)-4-oxo-4H-1-benzopyran-2-carboxylic acid, sodium salt A solution of 1.7 parts of 8-allyl-5-(2-hydroxypropoxy)-4-oxo-4H-1-benzopyran-2-carboxylic acid hemihydrate and 0.42 parts of sodium bicarbonate in 25 parts of water was prepared, filtered and freeze-dried to give 1.8 parts of 8-allyl-5-(2-hydroxypropoxy)-4-oxo-4H-1-benzopyran-2-carboxylic acid, sodium salt.

EXAMPLE 2

6,8-Di-t-butyl-4-oxo-4H-1-benzopyran-2-carboxylic acid a. 6,8-Di-t-butyl-4-oxo-4H-1-benzopyran-2-carboxylic acid A mixture of 5 parts of 2,4-di-t-butylphenol, 3.55 parts of acetylene dicarboxylic acid dimethyl ester and four drops of benzyl-trimethylammonium hydroxide were heated on a steam bath for 20 min. The 2,4-di-t-butylphenoxyfumaric acid dimethyl ester formed was hydrolysed by heating with 2.8 parts of sodium hydroxide in 15 parts by volume of water and 8 parts by volume of methanol. The hydrolysis was complete when one layer was obtained. The methanol was boiled off and the solution was cooled and acidified with concentrated hydrochloric acid. The crude 2,4-di-t-butylphenoxyfumaric acid was liberated as an oil, and was extracted into ether. This acid was purified by extraction with sodium bicarbonate solution which was washed well with ether. Acidification of the sodium bicarbonate solution gave the purified fumaric acid which was extracted again into ether. The dried ether extracts were evaporated to give the fumaric acid as an oil.

The di-t-butylphenoxyfumaric acid was cyclised by the cautious addition of 11 parts by volume of chlorosulphonic acid at 5°C. The mixture was kept for 20 min. at room temperature and then poured into water. The product which solidified, was washed well with petroleum ether (b.p. 40°–60°) then crystallised from aqueous ethanol to give 2.8 parts of 6,8-di-t-butyl-4-oxo-4H-1-benzopyran-2-carboxylic acid, melting point 230°–232°C.

Analysis:
Found: C, 71.4; H, 7.42%;
$C_{18}H_{22}O_4$ requires: C, 71.5; H, 7.33%.

b. 6,8-Di-t-butyl-4-oxo-4H-1-benzopyran-2-carboxylic acid, sodium salt

To 5.5 parts of 6,8-di-t-butyl-4-oxo-4H-1-benzopyran-2-carboxylic acid was added 1.4 parts of sodium bicarbonate in 150 parts by volume of water. The mixture was gently heated on a steam bath until nearly all the acid had dissolved. The neutral solution was filtered and freeze-dried to give 5 parts of 6,8-di-t-butyl-4-oxo-4H-1-benzopyran-2-carboxylic acid, sodium salt.

EXAMPLE 3 a. 6,8-Di-tert-butyl-4-oxo-4H-1-benzopyran-2-carboxylic acid, piperidine salt A solution of 5.0 parts of 6,8-di-tert-butyl-4-oxo-4H-1-benzopyran-2-carboxylic acid in 1.7 parts of piperidine and 50 parts of water was filtered and freeze-dried. The resultant pale yellow powder was washed with hot petroleum ether (b.p. 60°–80°C), giving 5.6 parts of 6,8-di-tert-butyl-4-oxo-4H-1-benzopyran-2-carboxylic acid, piperidine salt as a colourless powder, melting point 191°–194°C, (decomposition).

Analysis
Found: C, 71.5; H, 8.65; N, 3.57%
$C_{23}H_{35}NO_4$ requires: C, 71.29; H, 8.58; H, 3.61%

Spectral confirmation

NMR showed the 3-proton of the benzopyran ring as a singlet at 3.23τ, and broad signals at 7.05τ and 8.60τ were assigned to the piperidine ring protons (solvent: deuterium oxide).

b. 6,ε-Di-tert-butyl-4-oxo-4H-1-benzopyran-2-carboxylic acid, ethylamine salt 5.0 parts of 6,8-di-tert-butyl-4-oxo-4H-1-benzopyren-2-carboxylic acid were added to a mixture of 1.5 parts of 70% aqueous ethylamine and 50 parts of water. The resultant pale yellow solution was filtered and freeze-dried, and the resulting solid was washed with ether to afford 5.3 parts of 6,8-di-tert-butyl-4-oxo-4H-1-benzopyran-2-carboxylic acid, ethylamine salt as a colourless powder, melting point 205°–206°C (decomposition).

Analysis
Found: C, 69.2; H, 8.72; N, 3.74%
$C_{20}H_{29}NO_4$ requires: C, 69.13; H, 8.41; N, 4.03%

Spectral confirmation

The 3-proton of the benzopyran ring gave an NMR singlet at 0.20τ, and the N-ethyl group gave a quartet at 7.00τ and a triplet at ca. 8.80τ (Solvent: deuterium oxide).

EXAMPLE 4

6-Allyl-5-hydroxy-4-oxo-4H-1-benzopyran-2-carboxylic acid a. 2-Allyloxy-6-hydroxyacetophenone

A mixture of 15.2 parts of 2,6-dihydroxyacetophenone, 12.1 parts of allyl bromide and 13.8 parts of potassium carbonate in 100 parts of acetone was stirred and refluxed for 7 hours. The acetone was evaporated and water, dilute hydrochloric acid and ether were added.

The ethereal layer was separated, dried and evaporated to leave a yellow oil. This oil was distilled and the fraction boiling at 128°–132°C at 0.15 mms of mercury was collected. This oil solidified on cooling but thin layer chromatography showed it to be a mixture of product and starting material. The mixture was chromatographed on alumina using ether as eluent. Evaporation of the ether gave a yellow solid which crystallised from petroleum ether (b.p. 40°–60°C) to give 10.0 parts of 2-allyloxy-6-hydroxyacetophenone as yellow needles, melting point 45.5°–46.5°C.

Analysis:
Found: C, 68.4; H, 5.95%;
$C_{11}H_{12}O_3$ requires: C, 68.73; H, 6.29%.

b. 5-Allyloxy-4-oxo-4H-1-benzopyren-2-carboxylic acid ethyl ester

To a stirred solution of 1.2 parts of sodium in 35 parts of ethanol was added a solution of 3.85 parts of 2-allyloxy-6-hydroxyacetophenone and 10 parts of diethyl oxalate in 50 parts of diethyl ether. The mixture was stirred and refluxed for 5 hours, then poured into 500 parts of diethyl ether.

The product was then extracted into water (3 × 120 ml) and the aqueous solution was acidified with concentrated hydrochloric acid and extracted into chloroform (3 × 80 ml). The chloroform solution was dried over sodium sulphate and evaporated to leave a red oil. This oil was dissolved in 30 parts of ethanol, a few drops of concentrated hydrochloric acid were added and the solution was refluxed for 5 minutes. On cooling, 2.7 parts of a solid-crystallised out, melting point 95°–97°C which was shown to be a mixture of acid and ester by thin layer chromatography. This solid was washed with aqueous sodium bicarbonate solution and filtered to leave 2.5 parts of 5-allyloxy-4-oxo-4H-1-benzopyran-2-carboxylic acid ethyl ester, melting point 122°–123°C which was one spot on a thin layer chromatogram.

Analysis:
Found: C, 65.5; H, 5.10%;
$C_{15}H_{14}O_5$ requires: C, 65.7; H, 5.15%.

c. 6-Allyl-5-hydroxy-4-oxo-4H-1-benzopyran-2-carboxylic acid ethyl ester 3.44 Parts of 5-allyloxy-4-oxo-4H-1-benzopyran-2-carboxylic acid ethyl ester was heated at 200°C for 1½ hours. On cooling, the mass solidified and was then dissolved in ether and chromotographed on alumina using ether as eluent. The ethereal solution was concentrated whence 2.5 parts of 6-allyl-5-hydroxy-4-oxo-4H-1-benzopyran-2-carboxylic acid ethyl ester crystallised as yellow plates, melting point 99°–100°C.

Analysis:
Found: C, 65.5; H, 5.25%;
$C_{15}H_{14}O_5$ requires: C, 65.69; H, 5.15%.

d. 6-Allyl-5-hydroxy-4-oxo-4H-1-benzopyran-2-carboxylic acid

A suspension of 2.0 parts of 6-allyl-5-hydroxy-4-oxo-4H-1-benzopyran-2-carboxylic acid ethyl ester in aqueous sodium bicarbonate solution was stirred and heated at 100°C till solution was complete. The solution was treated with charcoal, filtered and acidified with dilute hydrochloric acid to give a yellow precipitate. This solid was crystallised from ethanol to give 0.84 parts of 6-allyl-5-hydroxy-4-oxo-4H-1-benzopyran-2-carboxylic acid as yellow needles, melting point 222°–224°C.

Analysis:
Found: C, 63.7; H, 4.16%;
$C_{13}H_{10}O_5$ requires: C, 63.4; H, 4.09%.

e. 6-Allyl-5-hydroxy-4-oxo-4H-1-benzopyran-2-carboxylic acid sodium salt

A solution of 0.7 parts of 6-allyl-5-hydroxy-4-oxo-4H-1-benzopyran-2-carboxylic acid and 0.24 parts of sodium bicarbonate in 50 parts of water was freeze-dried to give 0.7 parts of 6-allyl-5-hydroxy-4-oxo-4H-1-benzopyran-2-carboxylic acid sodium salt as a yellow solid.

EXAMPLE 5

6,8-Di-t-butyl-4-oxo-4H-1-benzopyran-2-carboxylic acid a. 3,5-Di-t-butyl-2-hydroxyacetophenone

A mixture of 20.6 parts of 2,4-di-t-butylphenol, 19.2 parts of acetic anhydride and 80 parts of boron trifluoride: acetic acid complex was heated for 2 hours at 100°C. After pouring into ice cold dilute hydrochloric acid the mixture was extracted with ether which was washed with water, sodium hydrogen carbonate solution and water. Addition of 40% sodium hydroxide solution caused the precipitation of sodium 2,4-di-t-butylphenate. The ether was decanted, washed with water, dried over magnesium sulphate and evaporated to a brown oil. Distillation under reduced pressure gave a pale yellow liquid: $b_{0.45}100°C$, which crystallised to give a compound, m.p. 45°–46°C.

Analysis:
Found: C, 77.7; H, 10.0%;
$C_{16}H_{24}O_2$ requires: C, 77.37; H, 9.74%.

b. 6,8-Di-t-butyl-4-oxo-4H-1-benzopyran-2-carboxylic acid ethyl ester

A solution of sodium ethoxide, prepared from 0.46 parts of sodium and 25 parts of ethanol, was added with stirring to a mixture of 1.24 parts of 3,5-di-t-butyl-2-hydroxyacetophenone and 1.35 parts of diethyl oxalate dissolved in 50 parts of diethyl ether. The mixture was stirred at reflux for two hours, poured into dilute hydrochloric acid and extracted with chloroform. The chloroform was washed with water and evaporated to a red oil. The oil was boiled for 10 minutes with ethanol containing 1.0 parts of concentrated hydrochloric acid. On cooling, the solution deposited crystals which were collected to yield 1.3 parts of 6,8-di-t-butyl-4-oxo-4H-1-benzopyran-2-carboxylic acid ethyl ester, m.p. 130°–131.5°C.

Analysis:
Found: C, 73.0; H, 8.01%;
$C_{20}H_{26}O_4$ requires: C, 72.7; H, 7.93%.

c. 6,8-Di-t-butyl-4-oxo-4H-1-benzopyran-2-carboxylic acid sodium salt

To a chilled solution of 1.02 parts of 6,8-di-t-butyl-4-oxo-4H-1-benzopyran-2-carboxylic acid ethyl ester in 100 parts of ethanol was added 3.1 parts of N sodium hydroxide solution. After the solution had been stirred at room temperature for one hour the solvent was evaporated and the remaining solid was triturated with ether and filtered off to yield 0.93 parts of 6,8-di-t-butyl-4-oxo-4H-1-benzopyran-2-carboxylic acid sodium salt.

EXAMPLE 6

5-(3-Methyl-n-butoxy)-8-n-propyl-4-oxo-4H-1-benzopyran-2-carboxylic acid a. 8-Allyl-5-(3-methyl-n-butoxy)-4-oxo-4H-1-benzopyran-2-carboxylic acid, ethyl ester A solution of 53 parts of 8-allyl-5-(3-methyl-n-butoxy)-4-oxo-4H-1-benzopyran-2-carboxylic acid in 750 parts of ethanol containing 2.0 parts of concentrated sulphuric acid was heated under reflux for 20 hours. The ethanol was removed by distillation and a solution of the residual oil in chloroform was washed with aqueous sodium bicarbonate solution and water. After drying, the chloroform solution was evaporated to leave an oil. This oil was dissolved in diethyl ether. On standing 45 parts of 8-allyl-5-(3-methyl-n-butoxy)-4-oxo-4H-1-benzopyran-2-carboxylic acid, ethyl ester crystallised as yellow needles, melting point 104°–105°C.

Analysis:
Found: C, 69.70; H, 7.22%;
$C_{20}H_{24}O_5$ requires: C, 69.75; H, 7.02%.

Spectral confirmation

Molecular weight = 344 by mass spectrometry. NMR (CDCl₃ solution) showed the ethyl ester protons as a quartet and triplet at 5.63τ and 8.62τ respectively.

b. 5-(3-Methyl-n-butoxy)-8-n-propyl-4-oxo-4H-1-benzopyran-2-carboxylic acid

A suspension of 12.05 parts of 8-allyl-5-(3-methyl-n-butoxy)-4-oxo-4H-1-benzopyran-2-carboxylic acid, ethyl ester in 225 parts of ethanol was treated with 0.2 parts of 5% palladium/charcoal catalyst and hydrogenated at a pressure of 4 atmospheres. After 30 minutes the hydrogen uptake ceased and the reaction mixture was filtered. The volume of the filtrate was reduced and then water was added. On standing 10.2 parts of 5-(3-methyl-n-butoxy)-8-n-propyl-4-oxo-4H-1-benzopyran-2-carboxylic acid, ethyl ester crystallised as yellow needles, melting point 64.5°–65°C. This material was stirred with a hot aqueous solution of sodium bicarbonate containing some ethanol for 2 hours. The resulting solution was cooled, washed with diethyl ether and acidified with dilute hydrochloric acid. The yellow precipitate was collected and crystallised from aqueous ethanol to give 7.2 parts of 5-(3-methyl-n-butoxy)-8-n-propyl-4-oxo-4H-1-benzopyran-2-carboxylic acid as yellow needles, melting point 166°–167°C.

Analysis:
Found: C, 67.50; H, 6.97%;
$C_{18}H_{22}O_5$ requires: C, 67.90; H, 6.97%.

Spectral confirmation

Molecular weight = 318 by mass spectrometry. Infra-red showed the acid carbonyl absorption at 1740 cm$^{-1}$ and the benzopyran ring carbonyl absorption at 1640 cm$^{-1}$.

NMR showed the 3-proton of the benzopyran ring as a singlet at 3.4τ.

c. 5-(3-Methyl-n-butoxy)-8-n-propyl-4-oxo-4H-1-benzopyran-2-carboxylic acid, sodium salt A mixture of 4.77 parts of 5-(3-methyl-n-butoxy)-8-n-propyl-4-oxo-4H-1-benzopyran-2-carboxylic acid and 1.26 parts of sodium bicarbonate was dissolved in 100 parts of water. The solution was filtered and freeze-dried. The hygroscopic solid was crystallised from ethanol to give 3.3 parts of 5-(3-methyl-n-butoxy)-8-n-propyl-4-oxo-4H-1-benzopyren-2-carboxylic acid, sodium salt as a white solid.

Spectral confirmation

Infra-red showed the carboxylate ion as a broad absorption about 1620 cm$^{-1}$.

NMR showed the 3-proton of the benzopyran ring as a singlet at 3.48τ.

EXAMPLE 7

5-(3-Methyl-n-butoxy)-8-n-propyl-4-oxo-4H-1-benzopyran-2-carboxylic acid a. 2-Hydroxy-4-(3-methyl-n-butoxy)propiophenone

A mixture of 116 parts of 2,4-dihydroxypropiophenone, 151 parts of isoamyl bromide and 140 parts of potassium carbonate in 300 parts of acetone were stirred and heated under reflux for 3 days. The reaction mixture was cooled, filtered and the filtrate was evaporated to dryness in vacuo. The resulting oil was dissolved in 500 parts of ether and 200 parts of 2N hydrochloric acid. The ether solution was washed with 100 parts of 2N hydrochloric acid, 6 lots of 50 parts of 5% aqueous sodium hydroxide solution, water, 2N hydrochloric acid, water, dried over anhydrous magnesium sulphate, filtered and evaporated to dryness in vacuo. The resulting colourless oil rapidly crystallised to give 108 parts of 2-hydroxy-4-(2-methyl-n-butoxy)propiophenone as a white solid, melting point 43.5°-44.0°C.

Analysis:
Found: C, 70.79; H, 8.42%;
$C_{14}H_{20}O_3$ requires: C, 71.16; H, 8.53%.

Spectral confirmation

Molecular weight = 236 by mass spectrometry.

N.m.r. showed only one hydroxyl proton at −2.55τ in carbon tetrachloride, characteristic of a hydrogen bonded phenol.

b. 5-(3-Methyl-n-butoxy)-2-propylphenol 100 parts of zinc wool, 10 parts of mercuric chloride, 5 parts of concentrated hydrochloric acid and 150 parts of water were shaken together for 5 minutes. The aqueous layer was decanted and the amalgamated zinc was covered with 150 parts of water and 200 parts of concentrated hydrochloric acid. A solution of 47.2 parts of 2-hydroxy-4-(3-methyl-n-butoxy)propiophenone in 200 parts of dioxan were added and the mixture was heated under reflux overnight. The reaction mixture was filtered, cooled and extracted with 4 lots of 100 parts of ether. The latter were combined and washed with 5 lots of 500 parts of water, dried over magnesium sulphate, filtered and evaporated to dryness in vacuo to a colourless oil, which solidified to give 43.7 parts of 5-(3-methyl-n-butoxy)-2-propyphenol as a colourless crystalline solid, melting point 40.0°-40.5°

Analysis
Found: C, 75.94; H, 9.78%;
$C_{14}H_{22}O_2$ requires: C, 75.63; H, 9.97%.

Spectral confirmation

Molecular weight = 222 by mass spectrometry.

N.m.r. displayed the presence of the propyl group and the phenolic hydroxy proton now appered at 4.05τ

The infra-red spectrum showed an intense broad O—H str peak at 3420 cm$^{-1}$ and two resolved peaks at 1620 and 1595 cm$^{-1}$ for the aromatic C=C stretch.

c. 5-(3-Methyl-n-butyoxy)-8-n-propyl-4-oxo-4H-1-benzopyran-2-carboxylic acid i. 22.2 Parts of 5-(3-methhyl-n-butyxoy)-2-propylphenol were dissolved in 14.2 parts of dimethyl acethyl acetylene dicarboxylate followed by addition of 0.25 parts of benzyl trimethylammonium hydroxide. The mixture was heated at 100° C for 45 minutes, after which 45 parts of 25% aqueous sodium hydroxide solution were added and the heating at 100° C was continued for a further 2½ hours. The resulting homogeneous solution was cooled and acidified to pH 1 with 20% v/v sulphuric acid. The yellow precipitate, produced, was extracted with 4 lots of 200 parts of ether and the latter was washed with 2N sulphuric acid, water, dried over magnesium sulphate, filtered and evaporated to dryness in vacuo. The resulting yellow oil quickly solidified to give 30.9 parts of a yellow solid. Recrystallisation from ethyl acetate/petrol (b.p. 60°-80° C) afforded 23.9 parts of 1-[2-propyl-5-(3-methyl-n-butoxy)phenoxy]ethylene-1,2-dicarboxylic acid.

ii. 10 Parts of 1-[2-propyl-5-(3-methyl-n-butoxy) phenoxy]ethylene-1,2-dicarboxylic acid were dissolved in 92 parts of concentrated sulphuric acid and allowed to stand at room temperature for 30 minutes. The mixture was filtered through glass wool into stirred ice water and the resulting yellow-brown syrup was extracted with ethyl acetate. The latter was washe with 2N sulphuric acid, water, dried over magnesium sulphate, filtered and evaporated to dryness in vacuo toyield a brown oil, which crystallised from ethyl acetate/petrol (b.p. 60°-80° C). The yellow crystals were collected and dried in vacuo, giving 1.24 parts of 5-(3-methyl-n-butoxy)-8-propyl-4-oxo-4H-1-benzopyran-2-carboxylic acid, melting point 166°-167° C.

Spectral confirmation

This product was shown to be identical to that prepared in Example 6.

EXAMPLE 8

6,8-Di-n-propyl-4-oxo-1-benzopyran-2-carboxylic acid a. 6,8-Di-n-propyl-4-oxo-4H-1-benzopyran-2-carboxylic acid

A solution of 6.2 parts of 6,8-dially-4-oxo-4H-1-benzopyran-2-carboxylic acid in 100 parts of ethanol was hydrogenated at room temperature for 45 minutes at a pressure of 45 p.s.i. in the presence of 5% palladised charcoal. The solution was filtered and evaporated to afford 6.1 parts of 6,8-di-n-propyl-4-oxo-4H-1-benzopyran-2-carboxylic acid, melting pont 183°–184° C after recrystallization from a mixture of ethyl acetate and petroleum ether (b.p. 60°–80° C).

Analysis: Found: C, 70.0; H, 6.75%; $C_{16}H_{18}O_4$ requires: C, 70.05; H, 6.61%.

Spectral confirmation

Molecular weight = 274 by mass spectrometry.

IR acid carbonyl absoption occurred at 1725 cm$^{-1}$ and benzopyran carbonyl absorption at 1620 cm$^{-1}$.

The N.M.R. spectrum contained a singlet at 2.7τ due to the benzopyran ring 3-proton (solvent: deuterochloroform).

b. 6,8-Di-n-propyl-4-oxo-4H-1-benzoypyran-2-carboxylic acid, sodium salt

A mixture of 4.7 parts of 6,8-di-n-propyl-4-oxo-4H-1-benzopyran-2-carboxylic acid and 1.37 parts of sodium bicarbonate was dissolved in 50 parts of water. The filtered solution was freeze-dried to give 4.5 parts of 6,8-di-n-propyl-4-oxo-4H-1-benzopyran-2-carboxylic acid, sodium salt.

Spectral confirmation

IR carbonyl absorption occurred at 1620 cm$^{-1}$.

The N.M.R. spectrum showed a singlet at 3.3τdue to the benzopyran ring 3-proton (solvent: deuterium oxide).

EXAMPLE 9

5-(3-Methyl-n-butoxy)-4-oxo-4H-1-benzoypyran-2-carboxylic acid a. Ethyl 5-hydroxy-4-oxo-4H-1-benzopyran-2-carboxylate, thallium salt A freshly prepared solution of 164.8 parts of thallous ethoxide in 500 parts of chloroform was quickly added to a stirred solution of 160 parts of 5-hydroxy-4-oxo-4H-1-benzopyran-2-carboxylic acid, ethyl ester in 2000 parts of chloroform. A further 1000 parts of chloroform was added and the mixture was stirred for twenty minutes. The precipitated product was collected by filtration, washed with chloroform and dried to give 303 parts of ethyl 5-hydroxy-4-oxo-4H-1-benzopyran-2-carboxylate, thallium salt m.p. >300° C.

b. 5-(3-Methyl-n-butoxy)-4-oxo-4H-1-benzopyran-2-carboxylic acid

A stirred mixture of 21.67 parts of ethyl 5-hydroxy-4-oxo-4H-1-benzopyran-2-carboxylate, thallium salt and 99 parts of 1-iodo-3-methylbutane was refluxed for one hour. After cooling, chloroform was added to the reaction mixture and the insoluble thallium salts were removed by filtration. The chloroform filtrate was washed with cold N sodium hydroxide solution, then washed with water and the volatile components were removed by evaporation. Sodiumbicarbonte soluton was added to the oily residue obtained and the mixture was stirred at 100° C for 2 hours. After cooling, the solution ws extracted with chloroform and the aqueous layer was separated. This aqueous extract was acidified with 2H hydrochloric acid and the solid which precipitated was collected by filtration, washed with water and dried to give 6.16 parts of 5-(3-methyl-n-butoxy)-4-oxo-4H-1-benzopyran-2-carboxylic acid, m.p. 181°–183° C (after crystallistion from ethyl acetate/light petroleum.

Spectral confirmation

Molecular weight = 27% by mass spectroscopy $C_{15}H_{16}O_5$ requires 276

EXAMPLE 10

5-(3-Methyl-n-butoxy)-4-oxo-4H-1-benzopyrann-2-carboxylic acid

A mixture of 23.4parts of 5-hydroxy-4-oxo-4H-1-benzopyran-2-carboxylic acid, ethyl ester, 19.8 partsof 1-iodo-3-methylbutane, 11.65 parts of anhydrous potassium carbonate and 500 parts of acetone was refluxed for thirteen days. After cooling, the reaction mixture was filtered and the volatile components of the filtrate were removed by evaporation to give a residue which was dissolved in chloroform. The chloroform extract was washed with cold N sodium hydroxide solution, then with water and evaporated. The oily residue obtained was stirred in sodium bicarbonate solution at 100° C for 2 hour. After cooling, the solution was extracted with chloroform and the aqueous layer was separated. The aqueous extract was acidified with 2N hydrochloric acid and the mixture was extracted with chloroform. Evaporation of the chloroform gave 8.79 parts of 5-(3-methyl-n-butoxy)-4-oxo-4H-1-benzopyran-2-carboxylic acid m.p. 181°–183° C (after crystallisation from ethyl acetate/light petroleum.

Spectral confirmation ;p Molecular weight = 276 by mass spectroscopy. $C_{15}H_{16}O_5$ requires 276

EXAMPLE 11

5-(3-Methyl-n-butoxy)-4-oxo-4H-1-benzopyran-2-carboxylic acid

A mixture of 23.4 parts of 5-hydroxy-4-oxo-4H-1-benzopyran-2-carboxylic acid, ethyl ester, 39.6 parts of 1-iodo-3-methylbutane, 11.65 parts of anhydrous potassium carbonate and 500 parts of isobutylmethyl ketone was refluxed for six days. After cooling, the reaction mixture was filtered and the volatile components of the filtrate were removed by evaporation to give a residue which was dissolved in chloroform. The chloroform extract was washed with cold N sodium hydroxide solution, then with water and evaporated.

The oily residue obtained was stirred in sodium bicarbonate solution at 100° C for 4 hours. After cooling, the solution was extracted with chloroform and the aqueous layer was separated. The aqueous extract was acidified with 2N hydrochloric acid and the mixture was extracted with chloroform. Evaporation of the chloroform gave 7.05 parts of 5-(3-methyl-n-butoxy)-4-oxo-4H-1-benzopyran-2-carboxylic acid m.p. 179°–180° C (after crystallisation from ethyl acetate/light petroleum).

EXAMPLE 12

6,8-Di-t-butyl-4-oxo-4H-1-benzopyran-2-carboxylic acid a. 6,8-Di-t-butyl-2,3-dihydro-4-oxo-4H-1-benzopyran-2-carboxylic acid, ethyl ester A solution of 12.0 parts of 6,8-di-t-butyl-4-oxo-4H-1benzopyran-2-carboxylic acid, ethyl ester in 150 parts of ethanoo was hydrogenated, using Raney Nickel as catalyst, until one equivalent of hydrogen had been absorbed. The catalyst was removed by filtration and the ethanol was evaporated to give a residue which was chromatographed on silica gel. Careful elution with a 1:1 mixture of chloroform and light petroleum (b.p. 60°–80° C) gave 3.73 parts of 6,8-di-t-butyl-2,3-dihydro-4-oxo-4H-1-benzopyran-2-carboxylic acid, ethyl ester, m.p. 61°–63° C, as a yellow solid.

Spectral confirmation

Molecular weight = 332 by mass spectroscopy $C_{20}H_{28}O_4$ requires 332 b.
6,8-Di-t-butyl-2,3-dihydro-4-oxo-4H-1-benzopyran-2-carboxylic acid, ethyl ester i. 2,4-Di-t-butylphenoxyfumaric acid A mixture of 2060 parts of 2,4-di-t-butylphenol, 1040 parts by volume of acetylene dicarboxylic acid dimethyl ester and 10 parts of benzyltrimethylammonium hydroxide was heated on a steam bath until a rapid exothermic reaction had occurred. The mixture was cooled to room temperature and ether was added. The ether extract was washed with N sodium hydroxide solution, sodium chloride solution and water, then the ether was removed by evaporation. The residue obtained was refluxed for three hours with 5000 parts of 5N sodium hydroxide solution. After cooling the mixture to room temperature, the solid which precipitated was removed by filtration.

The filtration was evaporated under reduced pressure to give a residue which was extracted into ether. The stirred ethereal extract was acidified with concentrated hydrochloric acid, washed with sodium chloride solution and dried. 5000 parts of benzene were added and solvent was removed from the mixture by distillation until a head temperature of 67° C was obtained. The resulting solution on cooling to room temperature gave 1429 parts of 2,4-di-t-butyophenoxyfumaric acid as a yellow solid, m.p. 188° C (after recrystallisation from benzene).

Analysis: Found: C, 67.48; H, 7.53%; $C_{18}H_{24}O_5$ requires: C, 67.50; H, 7.50%.

Spectral confirmation

Molecular weight = 320 by mass spectroscopy.

ii. 2,4-Di-t-butylphenoxysuccinic acid 3400 parts of a 2½% sodium amalgam were added over 1 hour to a stirred solution of 320 parts of 2,4-di-t-butylphenoxyfumaric acid in 2200 parts of N sodium hydroxide solution. The reaction mixture was stirred for two hours further, then water was added to dissolve the white solid which had formed. The solution was decanted from the mercury, extracted with chloroform and the aqueous layer was separated.

Concentrated hydrochloric acid was added to the stirred aqueous extract until the solution was strongly acidic. The precipitated white solid was collected by filtration washed with water and dried to give 231 parts of 2,4-di-t-butylphenoxysuccinic acid, m.p. 177°–181° C.

Spectral confirmation

Molecular weight = 322 by mass spectroscopy $C_{18}H_{25}O_5$ requires 322 iii.
6,8-Di-t-butyl-2,3-dihydro-4-oxo-4H-1-benzopyran-2-carboxylic acid, ethyl ester A mixture of 50 parts of 2,4-di-t-butylphenoxysuccinic acid and 100 parts of concentrated sulphuric acid was stirred at room temperature for three hours. The resulting solution was poured into water, excess sodium bicarbonate solution was added and the basic solution was extracted with ether. The aqueous extract was acidified with concentrated hydrochloric acid and the product was extracted into ether. The ether extract yielded a residue which was esterified by refluxing for three hours with 200 parts of a 3% v/v solution of ethanol containing concentrated sulphuric acid. After cooling, water was added and the esterified product was extracted into ether. The ether extract was washed with sodium bicarbonate solution and water, dried and the ether was removed by evaporation. Chromatography of the resulting residue on silica gel, elutingwith a 3:2 mixture of chloroform and light petroleum (b.p. 40°–60° C), gave 1 part of 6,8-di-t-butyl-2,3-dihydro-4-oxo-4H-1-benzopyran-2-carboxylic acid, ethyl ester as a semi-solid.

Spectral confirmation

Molecular weight = 332 by mass spectroscopy. $C_{20}H_{28}O_4$ requires 332 c. 6,8-Di-t-butyl-4-oxo-4H-1-benzopyran-2-carboxylic acid, ethyl ester

A mixture of 3.32 parts of 6,8-di-t-butyll-2,3-dihydro-4-oxo-4H-1-benzopyran-2-carboxylic acid, ethyl ester and 1.84 parts of N-bromosuccinimide was refluxed in 150 parts of carbon tetrachloride for six hours. The solution was cooled and then washed with water. The carbon tetrachloride extract was dried and the solvent was removed by evaporation. The resulting brown residue was crystallised from light petroleum (b.p. 40°–60° C) to give 1.69 parts of 6,8-di-t-butyl-4-oxo-4H-1-benzopyran-2-carboxylic acid, ethyl ester, m.p. 130°–131.5° C. The ester was hydrolysed to the sodium salt using the process of Example 5.

EXAMPLE 13

6,8-Di-t-butyl-4-oxo-4H-1-benzopyran-2-carboxylic acid, ethyl ester

A mixture of 3.32 parts of 6,8-di-t-butyl-2,3-dihydro-4-oxo-4H-1-benzopyran-2-carboxylic acid, ethyl ester and 3.33 parts of selenium dioxide was refluxed in 35 parts of xlene for eight hours. The reaction mixture was cooled, ether was added and the insoluble inorganic products were removed by filtration. Evaporation of the volatile components of the filtrate gave abrown residue which crystallised from light petroleum (b.p. 40°–60° C) to give 1.54 parts of 6,8-di-t-butyl-4-oxo-4H-1-benzopyran-2-carboxylic acid, ethyl ester, m.p. 130°–131.5° C.

EXAMPLE 14

6,8-Di-t-butyl-4-oxo-4H-1-benzopyran-2-carboxylic acid, ethyl ester

A mixture of 3.32 parts of 6,8-di-t-butyl-2,3-dihydro-4-oxo-4H-1-benzopyran-2-carboxylic acid, ethyl ester and 9.9 parts of lead tetraccetate was refluxed in 30 parts of glacial acetic acid for 6.5 hours. A further 9.9 parts of lead tetracetate were added and the reflux was continued for another 3.25 hours. After cooling, the reaction mixture was extracted with ether. The ether extract was washed with sodium bicarbonate solution and water and was dried. Evaporation of the ether gave an oil which was chromotographed on silica gel using a 9:1 mixture of toluene and ethanol for elution. This yielded 0.23 parts of 6,8-di-t-butyl-4-oxo-4H-1-benzopyran-2-carboxylic acid, ethyl ester, m.p. 130°–131.5° C (after crystallisation from light petroleum (b.p. 40°–60° C). This product was shown by spectral means to be the same as that of Example 13.

EXAMPLE 15

6,8-Di-t-butyl-4-oxo-4H-1-benzopyran-2-carboxylic acid, ethyl ester

A mixture of 3.32 parts of 6,8-di-t-butyl-2,3-dihydro-4-oxo-4H-1-benzopyran-2-carboxylic acid, ethyl ester, 1.56 parts of triphenylmethyl perchlorate and 30 parts of acetic anhydride was heated at 100° C for 30 minutes. After cooling, the reaction mixture was poured into sodium bicarbonate solution and the resulting mixture was washed with water, dried and the ether was evaporated to give an oil which was chromatographed on silica gel using a 1:1 mixture of chloroform and light petroleum (b.p. 40°–60° C) for elution. This yielded 0.14 parts of 6,8-di-t-butyl-4-oxo-4H-1-benzopyran-2-carboxylic acid, ethyl ester, m.p. 130°–131.5° C (after crystallisation from light petroleum (b.p. 40°–60° C). This product was shown by spectral means to be the same as that prepared in Example 13.

EXAMPLE 16

5-(3-Methyl-n-butoxy)-4-oxo-4H-1-benzopyran-2-carboxylic acid

A mixture of 1.0 parts of 5-(3-methyl-n-butoxy)-4-oxo-4H-1-benzopyran-2-carbonitrile, 20 parts of dioxan and 20 parts of dilute hydrochloric acid was heated at reflux for 24 hours. The dioxan was evaporated, and the reaction mixture was extracted with chloroform. The chloroform layer was then extracted with saturated sodium bicarbonate solution which an acidification gave 0.30 parts of 5-(3-methyl-n-butoxy)-4-oxo-4H-1-benzopyran-2-carboxylic acid, melting point 180°–182° C. The melting point, IR spectrum and thin layer chromatographic properties of the product were identical with those of the compound prepared in Example 9.

EXAMPLE 17

6,8-Dipropyl-4-oxo-4H-1-benzoypyran-2-carboxylic acid

A mixture of 1.0 parts of 6,8-dipropyl-4-oxo-4H-1-benzopyran-2-carboxamide, 20 parts of glacial acetic acid, and 20 parts of a solution of hydrogen bromide (45% weight/volume) in glacial acetic acid was heated at reflux for 3 hours, then the organic layer with saturated sodium bicarbonate solution, followed by acidification of the bicarbonate layer, afforded 0.16 parts of 6,8-dipropyl-4-oxo-4H-1-benzopyran-2-carboxylic acid, melting point 183°–184° C (decomposition). The melting point, IR spectrum and thin layer chromatographic properties of this material were identical with those of the compound prepared in Example 8.

EXAMPLE 18

8-allyl-5-(3-methyl-n-butoxy)-4-oxo-4H-1-benzopyran-2-carboxylic acid

To a stirred solution of 5.0 parts of 8-allyl-5-(3-methyl-n-butoxy)-4-oxo-4H-1-benzopyran-2-carbonyl chloride in 50 parts of dichloroethane was added 10 parts of water. The mixture was stirred at 50° C for one hour then evaporated to dryness. The resulting solid was washed thoroughly with aqueous sodium bicarbonate solution. Acidification of the bicarbonate solution with concentrated hydrochloric acid gave a yellow precipitate which was crystallized from ethyl acetate to give 2.6 parts of 8-allyl-5-(3-methyl-n-butoxy)-4-oxo-4H-1-benzopyran-2-carboxylic acid, m.p. 198°–199° C.

EXAMPLE 19

5-(3-Methyl-n-butoxy)-4-oxo-benzopyran-2-carboxylic acid hydroxylamine salt

An alkaline solution of hydroxlaminewas prepared by mixing 4 parts of sodium hydrogen carbonate with 3.6 parts of hydroxylamine hydrochloride in 100 parts of refluxing ethanol; after 15 minutes the precipitated sodium chloride was filtered off.

To a stirred suspension of 5 parts of 5-(3-methyl n-butoxy-4-oxo-4H-1-benzopyran-2-carboxylic acid, in 50 parts of refluxing ethanol, was added 40 parts of the hydroxylamine filtrate. The mixture was stirred and refluxed for a further 15 minutes, allowed to cool, and the white solid was filtered off to yield 5 parts of 5-(3-methyl-n-butoxy)-4-oxo-4H-1-benzopyran-2-carboxylic acid hydroxylamine salt.

Analysis: Found: C, 57.89; H, 6.18;N, 4.46%; $C_{15}H_{19}NO_6$ requires: C, 58.24; H, 6.19; N, 4.53%.

EXAMPLE 20

6-Allyl-5-(3-methyl-n-butoxy)-4-oxo-4H-1-benzopyran-2-carboxylic acid ethylamine salt An aqueous solution containing 5 parts of 8-allyl-5-(3-methyl-n-butoxy)-4-oxo-4H-1-benzopyran-2-carboxylic acid and 1.07 parts of ethylamine (70% v/v) was filtered and freeze-dried to give5 parts of 8-allyl-5-(3-methyl-n-butoxy)-4-oxo-4H-1-benzopyran-2-carboxylic acid ethylamine salt hemihydrate as a pale yellow solid, m.p. 135°–137° C.

Analysis: Found: C, 64.35; H, 7.34; N, 3,48%; $C_{20}H_{27}NO_5.1/2H_2O$ requires: C, 64.90; H, 7.57; N, 3.79%.

EXAMPLE 21

8-Allyl-5-(3-methyl-n-butoxy)-4-oxo-4H-1-benzopyran-2-carboxylic acid piperidine salt A solution of 5 parts of 8-allyl-5-(3-methyl-n-butoxy)-4-oxo-4H-1-benzopyran-2-carboxylic acid and 1.35 parts of piperidinein 50 parts of ethanol was refluxed for 2 hours. The resulting solution was filtered and evaporated to an oil which was dissolved in dry benzene. The benzene solution was evaporated to give an oil which was triturated with petroleum ether (b.p. 40°–60° C) to give 6 parts of 8-allyl-5-(3-methyl-n-butoxy)-4-oxo-4H-1-benzopyran-2-carboxylic acid piperidine salt as a white solid m.p. 106°–107° C.

Analysis: Found: C, 68.81; H, 7.78; N, 3.49%; $C_{23}H_{31}NO_5$ requires: C, 68.59; H, 7.77; N, 3.30%.

EXAMPLE 22

8-Allyl-5-(3-methyl-n-butoxy)-4-oxo-4H-1-benzoypyran-2-carboxylic acid calcium salt To a solution of 4.98 g of 8-allyl-5-(3-methyl-n-butoxy)-4-oxo-4H-1-benzopyran-2-carboxylic acid sodium salt in 50 parts of water was added a saturated solution of 1.2 parts of calcium nitrate in water. The resulting calcium salt was filtered off, washed with water and dried to give 5 parts of 8-allyl-5-(3-methyl-n-butoxy)-4-oxo-4H-1-benzpyran-2-carboxylic acid calcium salt monohydrate as a white solid.

Analysis: Found: C, 62.89%; H, 5.91%; $C_{36}H_{38}CaO_{10}.H_2O$ requires: C, 62.80; H, 5.82%.

EXAMPLE 23

8-Allyl-5-(3-methyl-n-butoxy)-4-oxo-4H-1-benzopyran-2-carboxylic acid tris-(hydroxymethyl)methylamine salt A solution of 5.66 parts of 8-allyl-5-(3-methyl-n-butoxy)-4-oxo-4H-1-benzopyran-2-carboxylic acid and 2.16 parts of tris-(hydroxymethyl)methylamine in 50 parts of ethanol was refluxed for 2 hours. The solution was filtered and evaporated to an oil which was triturated with ether to give 7.1 parts of 8-allyl-5-(3-methyl-n-butoxy)-4-oxo-4H-1-benzopyran-2-carboxylic acid tris-(hydroxymethyl)methylamine salt hemihydrate as a pale yellow solid.

Analysis: Found: C, 59.52; H, 7.43; N, 3.08%; $C_{20}H_{31}No_8.1/2H_2O$ requires: C, 39.20; H, 7.16; N, 3.14.

EXAMPLE 24

6,8-Di-tert-butyl-4-oxo-4H-1-benzopyran-2-carboxylic acid ($\beta$-diethylamino)ethyl ester hydrochloride A mixture of 10 parts of 6,8-di-tert-butyl-4-oxo-4H-1-benzopyran-2-carboxylic acid sodium salt and 8 parts of ($\beta$-diethylamino)ethyl chloride was shaken for 1 hour in benzene and refluxed for a further 10 hours. After cooling the inorganic solid was filtered off and the filtrate was evaporated to leave an oil which was heated at 110° C at 15 mm pressure for 3 hours to remove any remaining ($\beta$-diethylamino)ethyl chloride. The oil was then dissolved in diethyl ether and to this solution was added ethereal hydrogen chloride. The resulting solid was filtered off and crystallised from dioxan/diethyl ether to give 7.01 parts of 6,8-di-tert-butyl-4-oxo-4H-1-benzopyran-2-carboxylic acid ($\beta$-diethylamino)ethyl ester hydrochloride hemihydrate as a white solid.

Analysis: Found C, 64.91; H, 8.23; N, 3.09%; $C_{24}H_{36}ClNO_4.1/2H_2O$ requires: C, 64.50; H, 8.06; N, 3.14%.

The structure was confirmed by nuclear magnetic resonance and mass spectroscopy.

EXAMPLE 25

8-Allyl-5-(3-methyl-n-butoxy)-4-oxo-4H-1-benzopyran-2-carboxylic acid($\beta$-diethylamino)ethyl ester hydrochloride A mixture of 10.14 parts of 8-allyl-5-(3-methyl-n-butoxy)-4-oxo-4H-1-benzopyran-2-carboxylic acid sodium salt and 8.13 parts of ($\beta$-diethylamino)ethyl chloride was refluxed in benzene for 10 hours. The inorganic material was then filtered off and the filtrate was evaporated under vacuum to leave an oil. The oil was heated for 3 hours at 110° C at 15 mm pressure to remove the last traces of ($\beta$-diethylamino)ethyl chloride. The residual oil was cooled and dissolved in diethyl ether. To this solution was added ethereal hydrogen chloride and the resulting solid was filtered off and crystallised from dioxan/diethyl ether to give 9.8 parts of 8-allyl-5-(3-methyl-n-butoxy)-4-oxo-4H-1-benzopyran-2-carboxylic acid ($\beta$-diethylamino)ethyl ester hydrochloride hemihydrate as a white solid m.p. 125° C over a range.

Analysis: Found: C, 61.67; H, 7.50; N, 3.02%; $C_{24}H_{34}ClNO_5.1/2H_2O$ requires: C, 61.95; H, 7.60; H, 3.04%.

The structure was confirmed by nuclear magnetic resonance and mass spectroscopy.

EXAMPLE 26

8-Allyl-5-(3-methyl-n-butoxy)-4-oxo-4H-1-benzopyran-2-carboxylic acid pivaloyloxymethoxy ester To a solution of 5.4 parts of chloromethyl pivalate in 60 parts of dry acetone were added 6 parts of 8-allyl-5-(3-methyl-n-butoxy)-4-oxo-4H-1-benzopyran-2-carboxylic acid sodium salt and 0.1 parts of sodium iodide. The mixture was refluxed for 10 hurs, cooled and evaporated to an oil which was dissolved in diethyl ether. The ethereal solution was filtered and evaporated under vacuum to give an oil which solidified when triturated with petroleum ether (b.p. 40°-60° C). The solid was filtered off and crystallised from petroleum ether (b.p. 60°-80° C) to give 4.5 parts of 8-allyl-5-(3-methyl n-butoxy)-4-oxo-4H-1-benzopyran-2-carboxylic acid pivaloyoxymethyl ester, m.p. 79°-80° C.

Analysis: Found: C, 66.70; H, 7.03%; $C_{24}H_{30}O_7$ requires: C, 67.0; H, 8.98%.

The structure was confirmed by nuclear magnetic resonance and mass spectroscopy.

EXAMPLE 27

Bis-[8-allyl-5-(3-methyl-n-butoxy)-4-oxo-4H-1-benzopyran-2-carboxylic acid]2-oxapropan-1,3-diyl ester To a suspension of 3 parts of 8-allyl-5-(3-methyl-n-butoxy)-4-oxo-4H-1-benzopyran-2-carboxylic acid sodium salt in 30 parts of dry acetone, were added 0.5 parts of 1,1-dichlorodimethyl ether and 0.1 parts of sodium iodide. The mixture was refluxed for 1 hour, cooled and filtered. The filtrate was evaporated to an oil which was dissolved in chloroform. The chloroform solution was filtered and evaporated. The resulting oil was triturated with ether to give a solid which was filtered off and crystallised from benzene/petroleum ether (b.p. 40°-60° C) to give 1 part of bis[8-allyl-5-3-methyl-n-butoxy)-4-oxo-4H-1-benzopyran-2-carboxylic acid]2-oxapropan-1,3-diyl ester, m.p. 120°-121° C.

Analysis: Found: C, 67.20; H, 5.18%; $C_{38}H_{42}O_{11}$ requires: C, 67.6; H, 6.20%.

The structure was confirmed by nuclear magnetic resonance and mass spectroscopy.

EXAMPLE 28

8-Allyl-5-tetrahydrofurfuryloxy-4-oxo-4H-1-benzopyren-2-carboxamide

Anhydrous ammonia gas was passed through a stirred solution of 38.4 parts of 8-allyl-5-tetrahydrofurfuryloxy-4-oxo-4H-1-benzopyren-2-carboxylic acid ethyl ester in 600 parts of anhydrous ethanol at 45° C for 3 hours. The resulting dark, reddish brown solution was cooled to 0° C. A white crystalline solid was formed, which was collected and dried in vacuo. 24.7 Parts of 8-allyl-5-tetrahydrofurfuryloxy-4-oxo-4H-1-benzoypyren-2-carboxamide were obtained, melting point 211.5°-213.5° C.

Analysis: Found: C, 65.70; H, 5.84; N, 4.25%; $C_{18}H_{19}NO_5$ requires: C, 65.64; H, 5.82; N, 4.25%.

Spectral confirmation

Molecular weight = 329 by mass spectrometry.
The N.m.r. spectrum showed the 3-proton of the benzoypyren ring as a singlet at 2.10τ and the exchangeable amide protons at 2.20τ in trifluoroacetic acid.

The infra-red spectrum displayed peaks at 3070 cm$^{-1}$ for the 3-proton (C-H str) and 1715 and 1690 cm$^{-1}$ for the 4-oxo (C=O str) and amide I band (C=O str) respectively.

EXAMPLE 29

The carboxylic acids shown in Table I were produced from the appropriate starting materials using the method of the Example Number quoted in the Table. The sodium salts of all of these acids were prepared by the process of Example 1(c).

TABLE I

| Compound | Method of Prep. Ex. No. | M.P. °C | ELEMENTAL ANALYSIS FOUND | |
|---|---|---|---|---|
| | | | C | H |
| 5-(3-Methyl-n-butoxy)-4-oxo-4H-1-benzopyran-2-carboxylic acid | 1.b) | 181–183 | 65.4 | 5.79 |
| 6,8-Diethyl-5-hydroxy-4-oxo-4H-1-benzopyran-2-carboxylic acid | 1.b) & 4.d) | 219–211 | 64.1 | 5.3 |
| 6,8-Diallyl-5-hydroxy-4-oxo-4H-1-benzopyran-2-carboxylic acid | 1.b) | 174–175 | 66.8 | 4.86 |
| 7-(2-Ethoxyethoxy)-6-hexyl-4-oxo-4H-1-benzopyran-2-carboxylic acid | 1.b) | 128–129 | 66.1 | 7.19 |
| 8-Ethyl-5-tetrahydrofurfuryloxy-4-oxo-4H-1-benzopyran-2-carboxylic acid | 1.b) | 220–222 | 64.0 | 5.61 |
| 8-Allyl-5-tetrahydrofurfuryloxy-4-oxo-4H-1-benzopyran-2-carboxylic acid | 1.b) | 186–187 | 65.05 | 5.46 |
| 8-Ethyl-5-(3-methyl-n-butoxy)-4-oxo-4H-1-benzopyran-2-carboxylic acid | 1.b) | 205–207 | 66.8 | 6.75 |
| 8-Allyl-5-(5-methyl-n-butoxy)-4-oxo-4H-1-benzopyran-2-carboxylic acid | 1.b) | 198–199 | 68.00 | 6.40 |
| 6,8-Diallyl-5-(3-methyl-n-butoxy)-4-oxo-4H-1-benzopyran-2-carboxylic acid | 1.b) | 121.5–123 | 70.8 | 6.89 |
| 6,8-Diallyl-4-oxo-4H-1-benzopyran-2-carboxylic acid | 1.b) | 179–182 | 71.3 | 5.27 |
| 5-(3-Ethyl-n-butoxy)-4-oxo-4H-1-benzopyran-2-carboxylic acid | 1.b) | 155–160 | 66.35 | 6.31 |
| 5-(3-Ethyl-n-hexyloxy)-4-oxo-4H-1-benzopyran-2-carboxylic acid | 1.b) | 146–148 | 67.55 | 6.86 |
| 5-n-Hexyloxy-4-oxo-4H-1-benzopyran-2-carboxylic acid | 1.b) | 156.5–157.5 | 66.35 | 6.26 |
| 4-Oxo-5-n-pentyloxy-4H-1-benzopyran-2-carboxylic acid | 1.b) | 171–172 | 65.2 | 6.01 |
| 6,8-Diethyl-5-(3-methyl-n-butoxy)-4-oxo-4H-1-benzopyran-2-carboxylic acid | 1.b) | 182.5–183.5 | 68.4 | 7.51 |
| 6,8-Diallyl-5-tetrahydrofurfuryloxy-4-oxo-4H-1-benzopyran-2-carboxylic acid | 1.b) | 155.5–156.5 | 68.1 | 6.07 |
| 6,8-Diethyl-5-tetrahydrofurfuryloxy-4-oxo-4H-1-benzopyran-2-carboxylic acid | 1.b) | 143.5–144.5 | 68.03 | 6.55 |
| 6,8-Dimethyl-5-(3-methyl-n-butoxy)-4-oxo-4H-1-benzopyran-2-carboxylic acid | 1.b) | 230 | 66.81 | 8.62 |
| 4-Oxo-6-phenyl-4H-1-benzopyran-2-carboxylic acid | 2 | 253–254 | 72.3 | 3.78 |

EXAMPLE 30

The esters shown in Table II were prepared from the appropriate starting materials by the process shown in the table.

TABLE II

| Compound | Method of Prep. Ex. No. | M.P. °C | ELEMENTAL ANALYSIS FOUND | |
|---|---|---|---|---|
| | | | C | H |
| 6,8-Diethyl-5-hydroxy-4-oxo-4H-1-benzopyran-2-carboxylic acid ethyl ester | 5.b) | 82–84 | 66.09 | 6.25 |
| 6,8-Diallyl-4-oxo-4H-1-benzopyran-2-carboxylic acid ethyl ester | 6.a) | 65–66 | 72.59 | 6.28 |
| 8-Allyl-5-tetrahydrofurfuryloxy-4-oxo-4H-1-benzopyran-2-carboxylic acid ethyl ester | 5.b)& 6.a) | 115.5–117 | 67.08 | 6.22 |
| 8-Allyl-5-(3-methyl-n-butoxy)-4-oxo-4H-1-benzopyran-2-carboxylic acid ethyl ester | 5.b)& 6.a) | 104–105 | 69.2 | 7.22 |
| 5-(3-Methyl-n-butoxy)-4-oxo-4H-1-benzopyran-2-carboxylic acid ethyl ester | 6.a) | 61–62.5 | 66.8 | 6.59 |

EXAMPLE 31

The amides, shown in Table III, were prepared from the corresponding ethyl esters by the method of Example 28.

TABLE III

| Compound | M.P. °C | ELEMENTAL ANALYSIS FOUND | | |
|---|---|---|---|---|
| | | C | H | N |
| 6,8-Di-t-butyl-4-oxo-4H-1-benzopyran-2-carboxamide | 255–257 | 71.88 | 7.88 | 4.6 |
| 5-(3-Methyl-n-butoxy)-4-oxo-4H-1-benzopyran-2-carboxamide | 170–171 | 64.6 | 6.24 | 4.9 |
| 8-Allyl-5-(3-methyl-n-butoxy)-4-oxo-4H-1-benzopyran-2-carboxamide | 191.5–193 | 68.7 | 6.67 | 4.32 |
| 6,8-Diallyl-4-oxo-4H-1-benzopyran-2-carboxamide | 199–200 | 71.10 | 6.00 | 5.01 |
| 8-Allyl-5-tetrahydrofurfuryloxy-4-oxo-4H-1-benzopyran-2-carboxamide | 211.5–213.5 | 65.7 | 5.84 | 4.25 |

EXAMPLE 32

The preparation of the acetophenone starting materials for many of the carboxylic acids and ethyl esters shown in Tables I and II are either given here in detail or are listed in Table IV.

a. 3-Ethyl-6-tetrahydrofurfuryloxy-2-hydroxyacetophenone

A mixture of 75 parts of 3-ethyl-2,6-dihydroxyacetophenone, 80 parts of tetrahydrofurfuryl methanesulphonate, 52 parts of potassium carbonate and 500 parts of N,N'-dimethylformamide was stirred and heated on a steam bath for 70 hours. The resulting dark solution was diluted with water and acidified with dilute hydrochloric acid. The precipitated oil was extracted with diethyl ether and the extract was evaporated to dryness under reduced pressure. A solution of the residual oil in diethyl ether was extracted with 5% aqueous sodium hydroxide solution. The alkaline solution was extracted with chloroform and the extract was washed with water, dried and evaporated. Petroleum ether (b.p. 40°–60° C9 was added to the residue and the solution ws decanted from some tarry material. Evaporation of the petrol solution gave 21 parts of 3-ethyl-6-tetrahydrofurfuryloxy-2-hydroxyacetophenone as an orange oil.

b. 3,5-Diallyl-2-hydroxyacetophenone

A mixture of 57.5 parts of 2-allyloxy-3-allylacetophenone and 45 parts of N,N'-diethylaniline was heated in a sand bath for 4 hours at a temperature of 220° C. After cooling, the reaction mixture was added to excess dilute hydrochloric acid and extracted with diethyl ether. The extract was extracted to afford a red oil which on distillation under vacuum gave 64 parts of 3,5-diallyl-2-hydroxyacetophenone, boiling point 100°–120° C at 1.2 mm mercury.

TABLE IV

| Compound | Method of Prop. Ex. No | PHYSICAL CHARACTERISTICS WHERE MEASURED |
|---|---|---|
| 2-Hydroxy-6-(3-methyl-n-butoxy)acetophenone | 1.a) | yellow oil |
| 4-(2-Ethoxyethoxy)-5-hexyl-2-hydroxyacetophenone | 32.a) | pale yellow oil |
| 3,5-Diethyl-2,6-dihydroxyacetophenone | 5.a) | m.p. 76–77° C |
| 3,5-Diallyl-2,6-dihydroxyacetophenone | 32.b) | m.p. 55–56° C |
| 3-Allyl-6-tetrahydrofurfuryloxy-2-hydroxyacetopheneone | 32.a) | pale yellow oil |
| 3-Ethyl-2-hydroxy-6-(3-methyl-n-butoxy)acetophenone | 1.a) | brown oil |
| 3-Allyl-2-hydroxy-6-(3-methyl-n-butoxy)acetophenone | 1.a) | yellow oil |
| 3,5-Diallyl-2-hydroxy-6-(3-methyl-n-butoxy)acetophenone | 1.a) | b.p. 147–150° C at 0.7 mm Hg |
| 2-(2-Ethyl-n-butoxy)-6-hydroxy-acetophenone | 1.a) | brown oil |
| 2-(2-Ethyl-n-hexyloxy)-6-hydroxy-acetophenone | 1.a) | yellow oil |
| 2-n-Hexyloxy-6-hydroxyacetophenone | 1.a) | |
| 2-Hydroxy-6-n-pentyloxyacetophenone | 1.a) | |
| 3,5-Diethyl-2-hydroxy-6-(3-methyl-n-butoxy)acetophenone | 1.a) | yellow oil |
| 3,5-Diallyl-2-tetrahydrofurfuryloxy-6-hydroxyacetophenone | 32.a) | |
| 3,5-Diethyl-2-tetrahydrofurfuryloxy-6-hydroxyacetophenone | 32.a) | |
| 2,6-Dihydroxy-3,5-dimethylacetophenone | 5.a) | m.p. 144–146.5° C |
| 6-Hydroxy-3,5-dimethyl-2-(3-methyl-n-butoxy)acetophenone | 1.a) | red oil |

EXAMPLE 33

8-Allyl-5-(3-methyl-n-butoxy)-4-oxo-4H-1-benzopyran-2-carboxylic acid, 2'-dimethylamino-prop-2'-yl ester hydrochloride To a suspension of 6.76 parts of 8-allyl-5-(3-methyl-n-butoxy)-4-oxo-4H-1-benzopyren-2-carboxylic acid sodium salt in 200 parts of dry benzene were added 5.42 parts of 2-chloro-2-dimethyl-aminomethyl propane. The mixture was refluxed for 10 hours, cooled and filtered. The filtrate was evaporated to an oil which was dissolved in diethy ether. The ethereal solution was filtered and evaporated to an oil which was then heated at 100° C for 6 hours under vacuum.

After dissolving the oil in ether an excess of ethereal hydrogen chloride solution was added. The resulting solid comprising 4 parts of 8-allyl-5-(3-methyl-n-butoxy)-4-oxo-4H-1-benzopyren-2-carboxylic acid, 2'-dimethylaminomethyl prop-2'-yl ester hydrochloride hydrate was filtered off, washed with ether and crystallized from benzene as a white solid m.p. 183°–184° C.

Analysis: Found: C, 61.75; H, 8.04; N, 2.82%; $C_{24}H_{34}ClNO_5 \cdot H_2O$ requires: C, 61.4; H, 7.67; N, 2.98%.

The structure was confirmed by nuclear magnetic resonance and mass spctroscopy.

EXAMPLE 34

6,8-Di-t-butyl-4-oxo-4H-1-benzopyren-2-carboxylic acid

A solution of 2.72 parts of 6,8-di-t-butyl-2-methyl-4-oxo-4H-1-benzopyren and 4.44 parts of selenium dioxide in a mixture of 60 parts of water and 250 parts of volume of dioxan was heated under gentle reflux for 12 hours. After cooling, the solution was filtered and the solvents were evaporated from the filtrate. The residue thus produced was dissolved in 250 parts by volume of chloroform and the resulting solution was extracted with 3 portions of 100 parts of a solution containing 5 parts of sodium bicarbonate in 100 parts of water. The combined aqueous washings were acidified with concentrated hydrochloric acid to give a solid which was crystallized from aqueous ethanol to give 6,8-di-t-butyl-4-oxo-4H-1-benzopyren-2-carboxylic acid, m.p. 230°–232° C.

EXAMPLE 35

6,8-Diethyl-5-hydroxy-4-oxo-4H-1-benzopoyren-2-carboxylic acid a. 3,5-Diethyl-2-hydroxy-6-methoxyacetophenone A mixture of 43.2 parts of 3,5-diethyl-2,6-dihydroxyacetophenone, 30 parts of methyl iodide, 15.2 parts of anhydrous potassium carbonate and 300 parts of acetone was refluxed for 2 days. After cooling, the reaction mixture was filtered and the volatile components of the filtrate removed by evaporation. Chromatography of the residue obtained on silica gel, eluting with 4:1 and 2:1 mixtures of light petroleum and ether, gave 32 arts of 3,5-diethyl-2-hydroxy-6-mehoxyacetophenone as an oil.

Spectral confirmation

Molecular weight = 222 by mass spectroscopy $C_{13}H_{18}O_3$ requires 222 b.
6,8-Diethyl-5-methoxy-4-oxo-4H-1-benzopyran-2-carboxylic acid

A solution of 13.8 parts of sodium in 300 parts of 3,5-diethyl-2-hydroxy-6-methoxyacetophenone and 99 parts by volume of diethyloxalate in 300 parts of ether. The reaction mixture was stirred at room temperature for 2½ hours and then poured into a stirred mixture of 100 parts of chloroform, 300 parts of water and 60 parts of concentrated hydrochloric acid. The chloroform layer was separated and the solvent removed by evaporation to give an oil which was refluxed with a 95% v/v solution of ethanol containing concentrated sulphuric acid for four hours. Evaporation of the ethanol gave a residue which was refluxed with excess sodium bicarbonate solution for one hour. After cooling, the mixture was acidified with concentrated hydrochloric acid and extracted with chloroform. Evaporation of the chloroform and trituration of the residue obtained with light petroleum gave 17.6 parts of 6,8-diethyl-5-methoxy-4-oxo-4H-1-benzopyran-2-carboxylic acid, m.p. 199°–200° C (after crystallization from chloroform/light petroleum).

Analysis: Found: C, 64.4; H, 5.9%; $C_{15}H_{16}O_5$ requires: C, 65.2; H, 5.8%.

Spectral confirmation

Molcular weight = 276 by mass spctroscopy. $C_{15}H_{16}O_5$ requires 276 c.
6,8-Diethyl-5-hydroxy-4-oxo-4H-1-benzopyran-2-carboxylic acid

A mixture of 5 parts of 6,8-diethyl-5-methoxy-4-oxo-4H-1-benzopyran-2-carboxylic acid and 130 parts by volume of 48% aqueous hydrobromic acid was refluxed for seven hours. The reaction mixture was cooled and excess sodium bicarbonate solution was added. The solution was acidified with concentrated hydrochloric acid and then extracted with chloroform. Evaporation of the chloroform gave a residue which on trituration with light petroleum gave 2.3 parts of 6,8-diethyl-5-hydroxy-4-oxo-4H-1-benzopyran-2-carboxylic acid, m.p. 218°–220° C (after crystallization from ethanol).

Analysis: Found: C, 63.8; H, 5.6%; $C_{14}H_{14}C_5$ requires: C, 64.1; H, 5.3%. cl Spectral confirmation Molecular weight = 262 by mass spectroscopy $C_{14}H_{14}O_5$ requires 262

EXAMPLE A

The procedure set out below may be sed to assess the effectiveness of a compound in inhibiting the release of the pharmacological mediators of anaphylaxis.

In this test, the effectiveness of the compounds in inhibiting the passive cutaneous anaphylactic reaction in rats is assessed. It as been proved that this form of test gives reliable qualitative indications of the ability of the compounds under test to inhibit antibody-antigen reactions in man.

In this test method Charles River France/Fisons bred rats (male or female) having a body weight of from 100 to 150 gms are infected subcutaneously at weekly intervals with N. brasiliensis larvae in doses increasing from about 2000 larvae per animal to 12,000 larvae per animal in order to establish the infection. After 8 weeks the rats are bled by heart puncture and 15–20 mls of blood are collected from each animal. The blood samples are then centrifuged at 3500 r.p.m. for 30 minutes in order to remove the blood cells from the blood plasma. The serum is collcted and used to provide a serum containing N. brasiliensis antibody. A pilot sensitivity test is carried out to determine the least quantity of serum required to give a skin weal in control animals in the test described below of 2 cm diameter. It has been found that optimum sensitivity of rats in the body weight range 100–130 gas is obtained using a serum diluted with eight parts of physiological saline solution. This diluted solution is called antibody serum A.

The antigen to eact with the antibody in serum A is prepared by removing N. brasiliensis worms from the gut of the infested rats, centrifuging the homogenate and collecting the supernatent liquor. This liquor is diluted with saline to give a protein content of 1 mg/ml and is known as solution B.

Charles River France/Fisons bred rats in the body weight range 100 to 130 gms are sensitized by intra dermal injection of 0.1 mls of serum A into the right flank. Sensitivity is allowed to develop for 24 hours and the rats are then injected intravenously with 1 ml/100 gms body weight of a mixture of solution B (0.25 mls), Evand Blue dye solution (0.25 mls) and the solution of the compound under test (0.5 mls with varying percentages of active matter). Insoluble compounds are administered as a separate intraperitoneal injection 5 minutes before intravenous administration of solution B and Evans Blue dye. For each percentage level of active matter in the solution under test five rats are injected. Five rats are used as controls in each test. The dosages of the compound under test are selected so as to give a range of inhibition values.

Thirty minutes after injection of solution B the rats are killed and the skins are removed and reversed. The intensity of the anaphylactic reaction is assessed by comparing the size of the characteristic blue weal produced by spread of the Evans Blue dye from the sensitizaion site, with the size of the weal in the control animals. The size of the weal is rated as 0 (no weal detected, i.e. 100% inhibition) to 4 (no difference in size of weal, i.e. no inhibition) and the percentage inhibition for each dose level calculated as:

% inhibition =

$$\frac{(\text{Control group score - treated group score}) \times 100}{\text{Control group score}}$$

The percentage inhibitions for the various dose levels are plotted graphically for each compound. From these graphs the dosage required to achieve a 50% inhibition of the anaphylactic reaction ($ID_{50}$) may be determined.

The compounds are also evaluated in the above manner using intestinal and gastric administration of the compound.

EXAMPLE B

| Tablet | | |
|---|---|---|
| | Compound of formula I, e.g. 8-allyl-5-(3-methyl-n-butoxy)-4-oxo-4H-1-benzopyran-2-carboxylic acid, | |
| sodium salt | | 500 mg |
| | Binder, e.g. powdered tragacanth | 1 to 3% |
| | Lubricant, e.g. magnesium stearate | 0.25 to 1% |
| | Disintegrating agent, e.g. potato starch | 5 to 10% |
| | Surfactant, e.g. di-octylsodium | |
| sulphosuccinate | | 0.25% |
| Example C | | |
| Capsule (Hard) | | |
| | Sodium salt of compound of formula I | 500 mg |
| | Granulating agent, e.g. gum or starch | |
| mucilage | | q.s. |
| | Lubricant, e.g. magnesium stearate | 0.25 to 1% |
| Example D | | |
| Capsule (Soft) | | |
| | Sodium salt of compound of formula I | 500 mg |
| | Polyethylene glycol 400 | q.s. |
| | Non-ionic surfactant, e.g. poloxy ethylene | |
| sorbitan mono-oleate | | q.s. |
| Example E | | |
| Suppository | | |
| | Sodium salt of compound of formula I | 500 mg |
| | Basis, e.g. polyethylene glycol 6,000 | 1 g |

We claim:
1. A composition useful for the prevention of asthmatic symptoms comprising an amount useful for the prevention of asthmatic symptoms of 6,8-di-t-butyl-4-oxo-4-H-1-benzopyran-2-carboxylic acid or a pharmaceutically acceptable salt, lower alkyl ester, ester with a di-lower alkylamine substituted lower alkanol, bis ester with a di-(hydroxy lower alkyl) ether or unsubstituted amide thereof, as active ingredient, in combination with a pharmaceutically acceptable carrier.

2. A composition according to claim 1 comprising from 0.17 to 600 mg. of active ingredient in unit dosage form.

3. A composition according to claim 1 comprising an effective amount of 6,8-di-t-butyl-4-oxo-4H-1-benzopyran-2-carboxylic acid.

4. A method for inhibiting the symptoms of asthma in a patient having asthma which comprises administering to said patient, an effective amount of 6,8-di-t-butyl-4-oxo-4H-1-benzopyran-2-carboxylic acid or a pharmaceutically acceptable alt, lower alkyl ester with a di-lower alkylamine substituted lower alkanol, bis ester with a di-(hydroxy lower alkyl) ether or unsubstituted amide thereof, as active ingredient, in combination with a pharmaceutically acceptable carrier.

* * * * *